US00PP21965P3

(12) United States Plant Patent

Lu et al.

(10) Patent No.: US PP21,965 P3

(45) Date of Patent: Jun. 7, 2011

(54) MUSCADINE GRAPE PLANT NAMED 'MAJESTY'

(50) Latin Name: ***Vitis rotundifolia* Michx.**
Varietal Denomination: Majesty

(75) Inventors: Jiang Lu, Tallahassee, FL (US); Zhong-bo Ren, Tallahassee, FL (US); Xia Xu, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 0 days.

(21) Appl. No.: 12/082,850

(22) Filed: Apr. 15, 2008

(65) Prior Publication Data

US 2010/0242143 P1 Sep. 23, 2010

(51) Int. Cl.
*A01H 5/00* (2006.01)

(52) U.S. Cl. ..... Plt./206

(58) Field of Classification Search ..... Plt./206, Plt./205

See application file for complete search history.

(56) References Cited

U.S. PATENT DOCUMENTS

| | | | |
|---|---|---|---|
| PP5,824 | P | 12/1986 | Ison |
| PP7,267 | P | 7/1990 | Ison |
| PP7,295 | P | 8/1990 | Ison |
| PP7,592 | P | 7/1991 | Ison |
| PP11,260 | P | 3/2000 | Lane |

*Primary Examiner* — June Hwu
*Assistant Examiner* — Louanne C Krawczewicz Myers
(74) *Attorney, Agent, or Firm* — Parks IP Law LLC; Collen Beard, Esq.

(57) ABSTRACT

A new and distinct cultivar of the muscadine grape plant, *Vitis rotundifolia* Michx., which has exceptionally good flavor, firm flesh texture with relatively thin skin, and a larger berry than the current grapes that are produced commercially. The vines of this cultivar are vigorous, productive and disease resistant.

1 Drawing Sheet

GOVERNMENT SUPPORT

This research was supported by Florida Department of Agriculture and Consumer Services grant contract number 000465.

BRIEF SUMMARY OF THE INVENTION

The present invention comprises a new and distinct plant cultivar of *Vitis rotundifolia* Michx., which has been given the name 'Majesty'. The following traits have been repeatedly observed and are the most pronounced characteristics of this new cultivar when grown in Florida, and which in combination distinguish it from existing cultivars:

1) Vigorous vine growth, high fruit yield, and disease resistant.
2) Very large red-black colored fruit, which is 3-4 grams more than the largest muscadine variety.
3) Very good flavor.
4) Low fruit rot and relatively low wet scar.

BRIEF DESCRIPTION OF THE DRAWINGS

The accompanying color photograph shows a representative section of a typical specimen of the new cultivar.

This photograph is a detailed view of several clusters of ripe berries, obtained by clipping away some foliage.

DETAILED DESCRIPTION

In the following description, color references are made to The Royal Horticultural Society Colour Chart (RHS) except where general terms of ordinary dictionary significance are used.

BACKGROUND OF THE INVENTION

The muscadine grape, *Vitis rotundifolia* Michx., is a popular fresh fruit grown in the Southeastern United States. In the North Florida climate, it ripens in late August when few other fruits are in season. The berries are large, as compared to other grape species, and are borne in small clusters of 5 -10. When fully ripe, the berries on some previously existing cultivars such as 'Dixieland' (U.S. Plant Pat. No. 4,771) are generally bronze, but the berries on other preexisting cultivars can range from red to black with slightly raised lenticels, giving a somewhat mottled appearance.

'Supreme' (U.S. Plant Pat. No. 7,267) is a muscadine grape cultivar introduced in the late 1980s for the fresh fruit market in the Southeastern United States. It was developed from a cross between the female variety 'Black Fry' (U.S. Plant Pat. No. 5,824) and the pollen parent 'Dixieland' made by Mr. W. G. Ison. 'Supreme's' distinguishing features were that it was an improved variety at the time of its release of the muscadine grape, and the large sized black berry. 'Black Fry' was developed from a cross between the female variety 'Fry' (unpatented) and the pollen parent variety 'Cowart' (unpatented), also made by Mr. Ison. 'Black Fry's' distinguishing features were that its characteristics, such as quality, shelf life, and sugar content were superior to both parents. 'Triumph' (unpatented) is a cross made by Mr. Fry in 1965. The original seedling was identified in 1971, and the cultivar has been grown commercially for over a decade. Two distinguishing characteristics of 'Triumph' are its prolific pollen production, making it an excellent planting adjacent to pistillate cultivars, and the high percentage of its berries which separate with a high dry stem scar (i.e., no tear in the berry at the point of detachment for the pedicel). Despite these distinguishing characteristics of 'Supreme', 'Fry' and Triumph', customers are always looking for a variety with even bigger berries. Furthermore, we have found that the yields for 'Supreme' and 'Fry' were inconsistent in different years and locations.

Thus, there has been a need to develop a new cultivar that has a berry size that is larger than the current muscadine variety and has a firm flesh texture with relatively thin skin and good flavor, which also retains important agronomic characteristics such as vigorous growth, disease resistance and very low fruit rot. Additionally, there is a need to develop a muscadine grape plant cultivar with a relatively low wet scar to minimize berry damage for the fresh fruit market.

Origin of the Invention

The plant of this invention, 'Majesty', was developed from an organized scientifically designed breeding program conducted in Tallahassee, Fla. 'Majesty' originated from a seeding population crossed between *Vitis rotundifolia* Michx. cultivars 'Supreme' (U.S. Plant Pat. No. 7,267) and 'Triumph' (unpatented) in 1997. The seedling was selected from a progeny of 36, and testing of the agronomic characteristics began in 2001 in Tallahassee, Fla. The new cultivar was asexually reproduced from cuttings taken from the original seedling and the new cultivar has been tested under the experimental designation O26-5-8. The unique features of the new cultivar have been retained.

Methods of Asexual Reproduction

'Majesty' was asexually reproduced in Tallahassee, Fla., utilizing standard mist propagation techniques. No hormones were used. Soft wood cuttings from the original 'Majesty' vine were taken in June and July, and two-node softwood cuttings were placed in a 50% sand and 50% peat moss medium. The cuttings were misted for 5 seconds in 10 minute intervals for a period of about 16 hours during the day. After rooting in four weeks, the cuttings were moved out of the mist bed to a shaded nursery, and the vines were fully established in two months.

Other methods of asexual reproduction are possible. One alternate method comprises layering, wherein the current season's growth is placed in a trench 4-6" deep at the base of the mother plant, still attached to the mother vine, and covered with moist material such as sphagnum moss. Rooting cuttings from the material in the trench can then be separated from the mother plant during the following dormant season.

Plant Characteristics

The following plant characteristics are relevant for plants that are five years old. Muscadine vines grown from seed will normally take three years to bloom and set fruits. The vine reaches peak production in four to five years. Commercially grown vines are produced from clonal propagation, which are rooted from the annual growing shoots. They can bloom and set fruits in the second year after planting, and will reach full fruit production in three to four years.

Vines: The vines of 'Majesty' grow vigorously, i.e., the growth of lateral canes on mature vines is at least 4 to 8 feet per growing season. The vines typically fill a 12 foot single-wire trellis by the end of the first growing season in Florida. The trunk caliper measurement at 12 inches above the soil line averages 4.3 inches for a typical five-year old vine.

Trunk: The 'Majesty' cultivar has tight, non-shedding bark with moderate brown color (RHS 165A).

Shoots: 'Majesty' has dark green (RHS 132A) shoots with average 3-6 cm internodes. New shoots from dormant buds typically produce inflorescences at the $3^{rd}$ and $4^{th}$ nodes. Inflorescences are compound panicles composed of 10 to 20 flower clusters, each containing 5 to 15 individual female flowers.

Buds: The development of shoots in the spring results from the emergence of compound buds on the canes. Each bud arises as an axillary bud meristem in each leaf axil of the shoot in the previous growing season. Potential fruiting clusters, also called inflorescences, are initiated within developing axillary buds the season prior to bloom. The inflorescences may be up to 10 cm long at bloom. The inflorescence is a panicle consisting of flowers arranged within variously branched dichasia. Thus, the main axis is terminated by a flower, as are each of the lateral branches. The flowers start to bloom in late April, and are at full bloom in early to mid May.

Canes: Lateral canes are semi-drooping and generally grow 6-8 feet or more in a season in Florida. The cane color ranges from dark green (RHS 132A) (younger cane, one year old) to moderate brown color (RHS 165A) (two year and older canes) and the bark is thin, hard and smooth, i.e., the bark does not separate from the trunk/stem. Cane diameter is 0.2 to 0.5 inches. Internode length ranges from 1.5 to 3.0 inches. Tendrils averaging 4.5 inches in length are unbranched and the pith discontinuous along the nodes.

Foliage: 'Majesty' has 2-3" small, round, unlobed leaves with 20-25 dentate margins and an acuminate point. Leaves average 3.5 inches in length and 2.5 in width. The leaves are nearly circular with broadly toothed margins, and glabrous on both upper and lower surfaces. Mature upper leaf surface are limpid green (RHS 135C) and somewhat shiny, while the lower leaf surfaces are paris green (RHS 1346) and are not as dark and less bright compared to the upper surface. The leaves become subglaborous at maturity and are deciduous. Petiole length equals or slightly exceeds the blade midrib length and the petiole sinus is shallow and wide angled. The petiole is dark green (RHS 132A).

Flowers: 'Majesty' bears pistillate (female) flowers, which require pollinators to set fruits. Flower are small (⅛"), indiscrete, and green (RHS 140A), borne in racemose panicles opposite leaves at the base of current season's growth. The petals are small (with the inflorescence less than 0.2 inches in diameter), which is typical for the species.

The non-functional anthers are chartreuse yellow (RHS 154C), and supported on short and deflected filaments at the base of the ovary. The flowers are short lived, lasting approximately 3 to 5 days. 'Majesty' typically blooms from April 25 through May 10 at Tallahassee, Fla. Successful pollination of 'Majesty' has been accomplished with 'Triumph', 'Alachua' (unpatented) and 'Cowart.' Any male and perfect flowers in the species can serve as a pollen source. Both wind and insects play an important role in the pollination of the flowers.

There are 5 each of sepals, petals, and stamens in dark green color (RHS 132A). Ovaries are superior and contain 2 locules each with 2 ovules. The calyptra, or cap is the corolla, in which the petals are fused at the apex; it abscises at the base of the flower and pops off at anthesis. Each cluster has about 10-30 flowers.

Fruit: The vines produce large, red-black colored fruit, which ripen in a 1 to 2 week period beginning around August 25 in Tallahassee, Florida. At maturity, the berries weigh approximately 16.5 grams each and average 15.2% soluble solids. The berries have firm flesh texture, aromatic flavor, and relatively thin edible skin. The berries are round to slightly elongated and range from 1.14 to 1.26 inches in diameter, containing an average of 3.1 seeds per berry. The fruit is borne in loose clusters of 3-15 grapes (average 5.8 berries per cluster).The berries have conspicuous lenticels giving them a somewhat mottled appearance. The berries separate from the pedicel with a relatively low wet scar, i.e., less than 30% of the berries are torn at the point of detachment from the pedicel. The red-black color of the 'Majesty' fruit falls into the purple-violet to violet groups (RHS 82A and 83A). This fruit color is distinct from the bronze fruit of 'Triumph,' and the black to deep red color of 'Supreme'. A comparison of the important fruit characteristics (size, soluble solids, berry cluster) and overall yield are presented in Table 1; these observations have been made annually over a three year period, except for the yield data, and the traits have been retained.

TABLE 1

Characteristics and Yield of 'Majesty' Compared to Three Fresh Market Muscadine Grape Cultivars in Tallahassee, Florida[1]

| Cultivar | Flower Type[2] | Berry Size (grams) | Soluble Solids (%) | Berries/ Cluster | lb/ Vine |
|---|---|---|---|---|---|
| Majesty | P | 16.5 | 15.2 | 5.8 | 73.4 |
| Alachua | SF | 7.4 | 16.3 | 7.7 | 56.0 |
| Fry | P | 10.3 | 17.0 | 5.9 | 40.5 |
| Supreme | P | 12.8 | 14.4 | 6.7 | 42.2 |

[1]The yield date (pound/vine is for 2007 only, while the other data are three year averages.
[2]Flower type: SF = self-fertile, P = pistillate.

Disease/ pest resistance or susceptibility: Like all other muscadine grapes, 'Majesty' grapes are much less bothered by diseases than other American and European grapes. It is highly disease resistant and essentially immune to phylloxera, nematodes, and Pierce's disease with very low fruit rot and relatively low wet scar. No severe fungal diseases have been observed except slight leaf spot.

What is claimed is:

1. A new and distinct variety of muscadine grape plant named 'Majesty', substantially as herein described and illustrated.

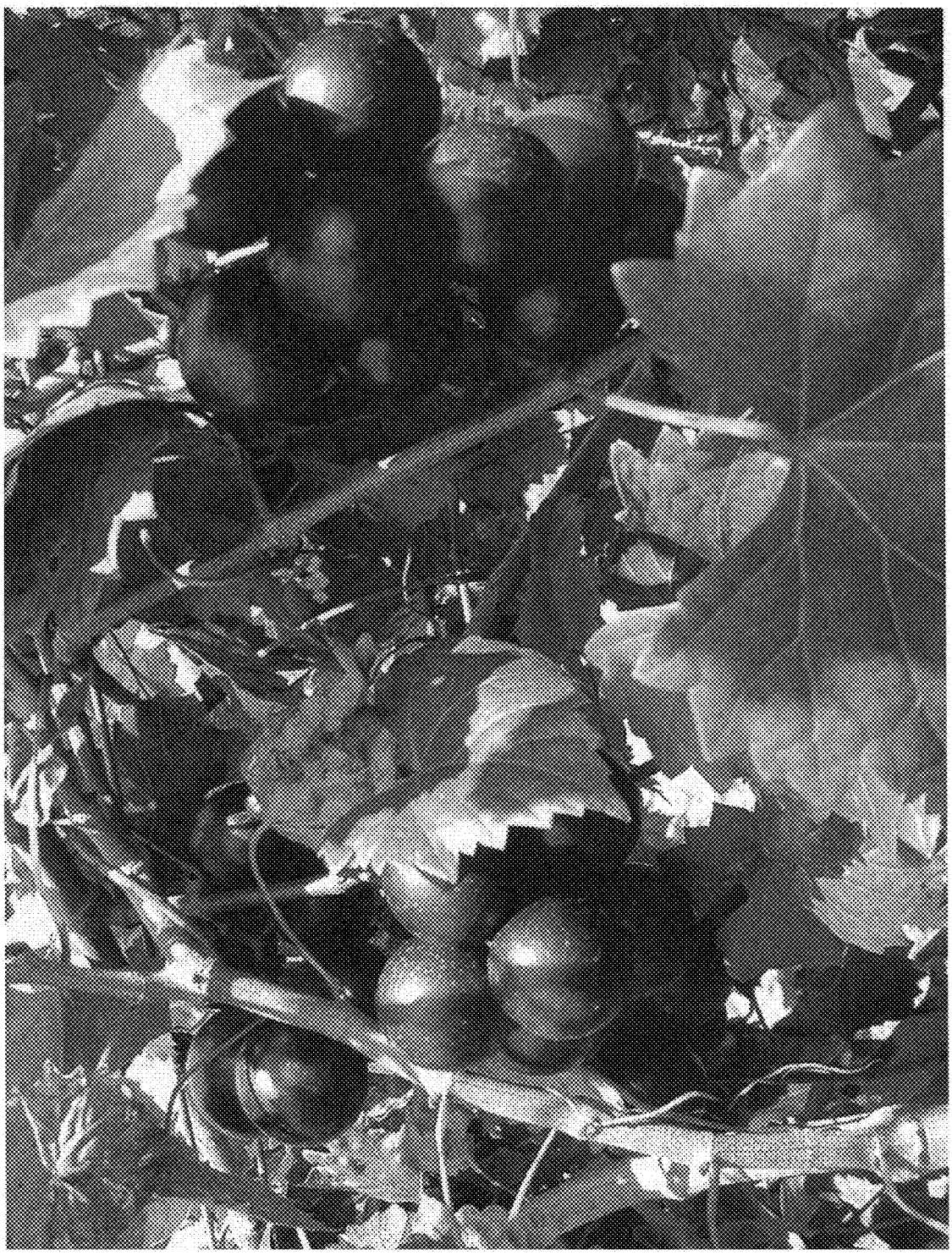

* * * * *